United States Patent [19]

Kao et al.

[11] Patent Number: 4,870,209

[45] Date of Patent: Sep. 26, 1989

[54] PROCESS FOR PURIFYING CRUDE 4-AMINOPHENOL

[75] Inventors: James T. F. Kao, Princeton Junction, N.J.; Dwight E. Raff, II, West Chester, Pa.

[73] Assignee: Noramco, Inc., Atlanta, Ga.

[21] Appl. No.: 43,787

[22] Filed: Apr. 29, 1987

[51] Int. Cl.$^4$ .................... C07C 85/26; C07C 85/11
[52] U.S. Cl. .................... 564/439; 564/416; 564/437
[58] Field of Search .................... 564/418, 437, 439

[56] References Cited

U.S. PATENT DOCUMENTS

| 3,694,508 | 9/1972 | Baron et al. | 564/418 |
| 3,845,129 | 10/1974 | Reid | 564/418 |
| 4,440,954 | 4/1984 | Clingan et al. | 564/439 |

FOREIGN PATENT DOCUMENTS 0041837 12/1981 European Pat. Off. ............ 564/437
61-56158 3/1986 Japan .

*Primary Examiner*—Glennon H. Hollrah
*Assistant Examiner*—Raymond Covington

[57] ABSTRACT

A process for the purification of crude 4-aminophenol which was prepared by the catalytic hydrogenation of nitrobenzene in aqueous sulfuric acid is described involving: adjusting the pH of an aqueous solution of crude 4-aminophenol to pH 4.0-5.0 at a temperature between 75° C. and 85° C.; mixing the aforesaid solution with toluene as the solvent, in order to extract various impurities and the dissolved nitrobenzene starting material; adjusting the pH of the resultant solution as required to maintain it at pH 4.0-5.0; allowing the resultant mixture to settle thereby forming a top organic layer and a bottom aqueous raffinate layer which raffinate contains 4-aminophenol and the by-product material, ortho-aminophenol; separating the two layers and repeatedly extracting the raffinate layer which toluene at pH 4.0-5.0 at a temperature of 75°-85° C. until most impurities have been removed from the resultant final raffinate; adding to the resultant raffinate, a charcoal decolorizing agent and a sodium sulfite type salt, which are then removed, leaving a filtrate which contains the 4-aminophenol and also the by-product ortho-aminophenol; adjusting the pH of said filtrate to pH 6.5-8.0 and cooling it to a temperature below 10° C.; separating the precipitated pure 4-aminophenol from the by-product ortho-aminophenol which remains in the solution.

12 Claims, 1 Drawing Sheet

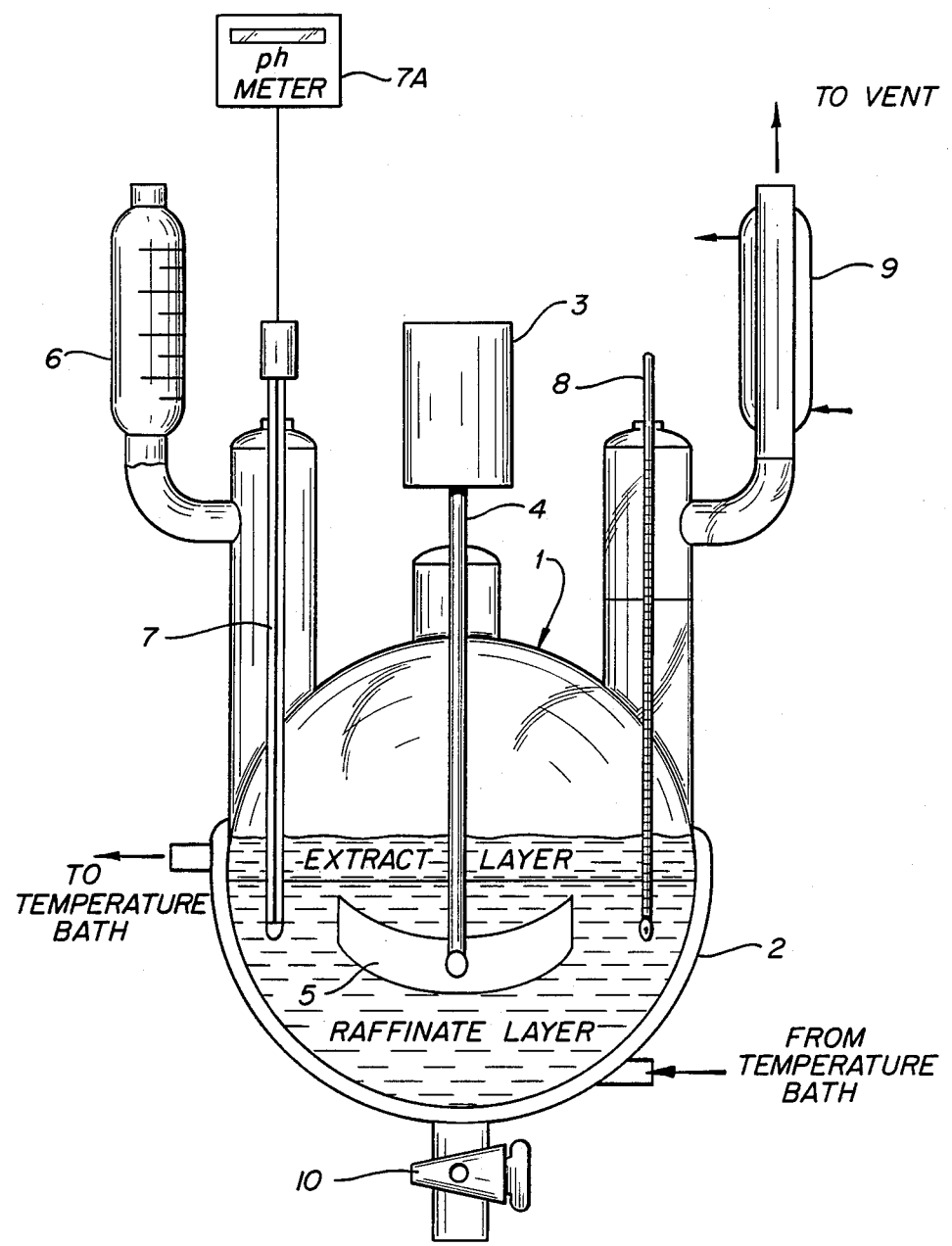

PROCESS FOR PURIFYING CRUDE 4-AMINOPHENOL

This invention relates to the purification of crude 4-aminophenol (p-aminophenol; PAP) obtained by the reduction of nitrobenzene.

BACKGROUND OF THE INVENTION 4-aminophenol (p-aminophenol; PAP) is obtained in crude form from the reduction of nitrobenzene. It is used commercially as an intermediate in the manufacture of acetaminophen (APAP; p-acetaminophenol). Since that material is a pharmaceutical, it must be pure. This requires that the crude PAP from which it is made must be purified to avoid undesirable by-products which cause color problems in the final acetaminophen.

Various processes for purifying crude PAP are known as shown in Baron et al. U.S. Pat. No. 3,694,508 and Yamamoto et al. U.S. Pat. No. 4,139,562. The Yamamoto et al. 4,139,562 patent process requires the use of excessive chemicals to manipulate pH values, and requires the use of a toxic solvent, aniline, to do extraction, which complicates disposal of the waste filtrate.

The Baron et al. process involves admixing, at a temperature above 25° C., an aqueous solution of the crude PAP with a water immiscible solvent (e.g., a lower alkyl acetate, benzene, toluene, or xylene) to dissolve substantially all the impurities, adjusting the pH of the resultant mixture to between 6.5 and 7.5, cooling the mixture to a temperature below 30° C., and separating the precipitated and purified PAP therefrom.

The present invention involves a different type of process than that taught by Baron et al. U.S. Pat. No. 3,694,508 giving better results, yields and quality by the use of a particular solvent toluene ([toluene is one of the many solvents taught, but is less preferred and not claimed by Baron et al.]), the use of a pH different than the pH of 6.5-7.5 taught by Baron et al., and the use of a lower cooling temperature than the 20°-30° C. taught by Baron et al.; and the use of different processing steps.

It has now been found that the process of purifying crude PAP (made by the catalytic hydrogenation of nitrobenzene in aqueous sulfuric acid, such as that process which is taught by Benner et al., U.S. Pat. Nos. 3,383,416 and described in said Baron et al. 3,694,508 patent, or that improved process which is described in Applicant's copending patent application (Ser. No. 43784) filed even date herewith) can be greatly improved over the prior art by steps involving such differences as: (a) the use of toluene as the solvent; (b) the use of a pH of 4.6-4.8, [which is contrary to the teachings of Baron et al. patent which uses pH of 6.5-7.5, and says (col. 4, line 7) that "At pHs below about 6.5, particularly below 6.2, some of the p-aminophenol is held in solution as a sulfuric acid salt and lost during the separation step.]; (c) separating the mixture to a raffinate (bottom layer) and an extract layer at an elevated temperature and (d) adjusting the pH to 7.2 and then cooling the raffinate layer to below 10° C. to separate pure 4-aminophenol.

The "raffinate" is the liquid phase left from the feed after being extracted by the solvent.

SUMMARY OF THE INVENTION

The present invention is a process for the purification of crude 4-aminophenol which was prepared by the catalytic hydrogenation of nitrobenzene in aqueous sulfuric acid, which involves the steps of admixing at a temperature of 75°-85° C. (preferably 80° C.) an aqueous solution of the crude 4-aminophenol with toluene as the solvent to extract various impurities and the dissolved nitrobenzene starting material while maintaining and adjusting the pH of the mixture to pH 4.0-5.0 preferably to pH 4.6-4.8, separating the raffinate layer and adjusting its pH to 6.5-8.0, preferably to pH 7.0-7.4 and most preferably to pH 7.2, cooling the mixture to a temperature below 10° C. (preferably 0° C. or below), and separating the precipitated and purified 4-aminophenol therefrom.

DETAILED DESCRIPTION OF THE INVENTION

The present invention involves the discovery of particular conditions under which by-products, starting materials and color bodies can be extracted from the starting crude in an organic phase, while retaining the desired PAP end product in an aqueous phase (raffinate) from which it can be separated by precipitation and obtained in pure form. The materials and conditions which are used in carrying out the process of this invention are:

The entire purification process is carried out in a manner to avoid exposure to oxygen, preferably under a nitrogen atmosphere. The crude 4-aminophenol (PAP), adjusted to pH 4.0-5.0, is mixed with toluene at a temperature ranging between about 75°-85° C., most preferably at 80° C. The pH is adjusted as required with ammonia (liquid ammonia i.e. anhydrous ammonia works best; aqueous ammonia is usable but the resultant yields are lower) to pH 4.0-5.0, preferably to pH 4.6-4.8 and most preferably is maintained as close to pH 4.65 as possible. After the mixing is stopped and the mixture is allowed to settle, two layers are formed. Most of the by-products, starting materials and color bodies (except for the by-product ortho-aminophenol) will now be in the top organic layer. The two layers are each separately removed from the extractor. The bottom aqueous raffinate layer, after sampling and analysis by High Performance Liquid Chromatography (HPLC method) is returned to the extractor. The extraction with toluene is repeated in the same way, as many times as is required. The analysis determines when the undesired materials have been removed.

At this point the use of charcoal, preferably activated carbon, for decolorization of the resultant final raffinate is desirable, as is the use of a material like sodium hydrosulfite which acts to both decolorize the PAP in the resultant final raffinate and protect it from reacting with oxygen. While sodium hydrosulfite ($Na_2S_2O_4$) is preferred, we can also use other types sodium sulfite salts i.e. sodium salts containing at least one tetravalent sulfur atom e.g. sodium bisulfite ($Na_2SO_3$), sodium disulfite ($Na_2S_2O_5$) and sodium pyrosulfite ($Na_2S_2O_5$). We will refer to these as "sodium sulfite type salts" for purposes of this invention.

After the charcoal and sodium sulfite type salts have been removed, the filtrate, which now contains mainly PAP and by-product ortho-aminophenol, is adjusted as required with ammonia (again, liquid anhydrous ammonia is preferred over aqueous) to pH 6.5-8.0, preferably to between pH 7.0 and 7.4 and most preferably to pH 7.2, after which the system is gradually cooled below 10° C., preferably to about 0° C. or lower, while maintaining said pH level. While temperatures which are very low (e.g. −5° C. and below) give best results, cost considerations make us prefer to use 0° C.

The pure PAP precipitates out (while the by-product ortho-aminophenol remains in the filtrate) and is filtered out, and rinsed with an aqueous solution containing a sodium sulfite type salt to remove any remaining color bodies. The pure PAP can be used wet to make APAP by acetylation, or can be dried and used for other purposes.

Preparation of Crude PAP

In a preferred embodiment of the invention, the crude 4-aminophenol (PAP) starting material which is purified by the purification procedure of the present invention, was obtained by the catalytic hydrogenation of nitrobenzene in aqueous sulfuric acid, which process is described in Applicant's copending patent application U.S. Ser. No. 43,784, filed even date herewith, and is also described in the following Preparation 1.

The nitrobenzene starting material used was a high quality commercial grade nitrobenzene free of thiophene and other sulfur-containing compounds and of any catalyst poisons.

The high quality commercial grade sulfuric acid used was treated with hydrogen peroxide prior to use to remove catalyst poisons. One percent by weight of a 30 percent hydrogen peroxide solution was added to the sulfuric acid, which was then stirred until gas bubbling ceased and the color and the sulfuric acid became water clear, which took about 2-4 hours.

The catalyst used was a 5 percent platinum on carbon, dry pack catalyst, the carbon support available from Engelhard Industries as CP-86.

The following procedure of Preparation 1 was then used to obtain the crude PAP starting material.

PREPARATION 1

A five liter, three neck, four-baffled round bottom flask (hydrogenator) equipped with a heating mantle, overhead mechanical stirring motor [the stirrer motor is controlled by a controller which has both speed and torque readouts and controls] driving a curved blade impeller, and an inlet for gas feed into the vapor space is charged with 1700 ml of deionized water at an initial temperature of between 20° C. and 23° C. Next, 217g of hydrogen peroxide pretreated 93% sulfuric acid (made as described previously) is added to the system with moderate agitation. The acid addition generates a fairly strong exotherm, raising the temperature of the solution to between 36° C. and 38° C. This provides a convenient point to start heating the system to the desired reaction temperature of 94° C. A variac setting of 80V gives heating at a suitable rate. Next, for the initial run in a series, 271 g of nitrobenzene is added. Addition of the nitrobenzene normally decreases the system temperature by about 1° C. For runs in a series using recycled catalyst, 40-50 g nitrobenzene would be recycled with the catalyst to aid handling and the charge of fresh nitrobenzene would be reduced accordingly. 2.25 ml of dodecyldimethyl amine or other surfactant is added and the system closed. A nitrogen purge with a flow rate of about 100 ml/min is commenced at this point to remove oxygen and any trace volatile catalyst poisons from the system. A constant positive pressure is maintained with a twelve inch water column in the gas exit bubbler. This is equivalent to a moderate, positive pressure of about 26 mmHg above atmosphere.

The agitation rate is increased to 700 rpm or higher and the nitrogen purge continued. Exceedingly vigorous agitation is very important. The power input was calculated from torque and speed readings. Adjustment of speed was made to achieve the desired power input, which is 0.01 horsepower per gallon or higher. For a five inch impeller, a speed of 700 rpm gives a power input of 0.0225. Agitator depth is another critical parameter. For a given power input, maximum gas-liquid interfacial area is generated with the agitator depth equal to 50% of the liquid depth. For practical purposes, the reaction rate is directly proportional to the power input and agitator position. After maintaining the initial nitrogen purge for ten minutes, 1.40 g of dry packed 5 % platinum on carbon catalyst is added through an emerging stream of nitrogen, rinsed in with 25 ml deionized water, the system resealed, and the 100 ml/min nitrogen purge continued for at least a further 10 minutes. During the period when reagents are being charged to the system, the temperature must be monitored carefully to ensure that it does not exceed 90° C. The heating variac should be adjusted, if necessary, to maintain the temperature below this point.

After completion of the nitrogen purge, addition of hydrogen gas begins. The initial demand can be up to 700 ml/min and the gas source must be able to maintain a positive system pressure at all times while meeting this flow rate. A major explosion may result if the system is allowed to generate a partial vacuum and suck air back into the reactor. The hydrogenation is exothermic and a mild exotherm which raises the temperature of the system by about 4° C. occurs as the reaction begins. The reaction is allowed to proceed to 75-85% conversion (indicated by hydrogen uptake) so that the catalyst remains sufficiently wetted by the unreacted nitrobenzene. This is achieved in 2-3 hours.

To terminate the hydrogenation reaction a final nitrogen purge is used. Initially, up to 700 ml/min of nitrogen may be required to maintain the system at positive pressure. The flow rate should gradually be reduced to 100 ml/min and agitation stopped. Increase the variac setting as needed to maintain a temperature of about 85° C. The aqueous layer [which contains the crude 4-aminophenol (PAP)]is pumped under nitrogen to a 3 liter jacketed flask (decanter) with bottom valve. The reactor jacket is hooked into a circulating bath at 80° C. A nitrogen atmosphere is maintained throughout the work-up procedure because the reaction mixture quickly colors if exposed to air.

The purification process which is the subject of the present invention is further described below.

THE DRAWING

The equipment in which the procedure of Example 1 was conducted, is as disclosed in FIG. 1. FIG. 1 is a schematic drawing of an extractor (decanter) 1 which is a 3 liter, three-neck, round bottom glass flask, where the bottom has a stop-cock fitted funnel 10, to act as a separatory funnel. The middle neck contains an overhead mechanical stirring motor 3 which drives a stirring rod 4 with a curved blade impeller 5 at its lower end. One side neck contains a pH electrode 7 (which is connected to a pH meter 7A) and also a feed bottle 6 to allow the crude starting material, toluene and ammonia to be added to the flask. The third neck containsa thermometer 8 and a condenser 9 vent. The flask is inside a jacket 2 permitting its contents to be heated or cooled with liquid from a temperature bath.

EXAMPLE 1

Under nitrogen atmosphere, the crude-PAP containing aqueous layer from Preparation 1 is pumped into the extractor of FIG. 1, where the reactor jacket contains 80° C. fluid. The pH of said aqueous layer from Preparation 1 which is now at 80° C., is then adjusted to 4.6–4.8 with liquid ammonia. About 80 ml (54 g) are normally required. It is then extracted four to seven times (until the color is clear and the extract phase remains colorless) with 300 ml(260.1 g) of toluene in order to remove dissolved impurities, i.e. aniline, nitrobenzene and oxydianiline (ODA). The pH must be adjusted periodically as the extraction proceeds because it will tend to drop as impurities are removed into the organic layer. The toluene extractions are combined and the toluene, nitrobenzene, and aniline are recovered by subsequent distillation. The nitrobenzene recovered in this step is recycled to the hydrogenator of Preparation 1. After the extraction cycle is completed, 10 gm of activated carbon is charged (for decolorization). 5.0 g of sodium hydrosulfite are also charged here for decolorization and to protect the product from reacting with oxygen. The charcoal is removed via filtration through a standard 12.5 cm Buchner filter using a #3 Whatman filter paper. The carbon cake is rinsed twice with 100 g aliquots of hot deionized water and discarded. The filtrate and wash are transferred back to the extractor flask. After a nitrogen atmosphere is reestablished over the reaction mixture, the pH is adjusted to 7.2 with liquid ammonia. About 30 ml (20.2 g) are normally required. The system is slowly cooled to 0° C. over a period of 1.5–2 hours and then held for 1 hour with the pH maintained at 7.2.

4-aminophenol is isolated by vacuum filtration, rinsed twice with two 200 g aliquots of cold 1% sodium hydrosulfite solution and sucked dry on a frit for several minutes. The material (which can be acetylated at this point to make APAP) was dried at 50° C. in vacuo overnight. The dried 4-aminophenol was white and stable, and weighted 139 g. The purity of 4-aminophenol as analyzed by the HPLC method is over 99%. This represents 68% isolated yield based on the nitrobenzene reacted.

EXAMPLE 2

EXPLANATION OF THE EXTRACTION DATA

Following the procedure of Example 1 the aqueous reaction mixture from Preparation 1 was charged to a 3 liter round bottom, agitated, glass flask (extractor). The content was agitated and heated to 80° C. The pH of the solution was adjusted by liquid ammonia to 4.6–4.8. A weighed amount of toluene (specified in Table I) was added and agitated for 30 minutes. The mixture was settled for 30 minutes and layers separated. Each layer was drained into a separate flask. The bottom aqueous raffinate layer was sampled, analyzed by HPLC method and charged back to the extractor. Extraction with toluene was repeated four more times. The pH value was checked and adjusted with ammonia, if necessary. The aqueous reaction mixture contains several solutes; i.e. the desired product-PAP; by-products-OAP (ortho aminophenol), ANL (aniline), ODA (oxydianiline), and starting material, NB (nitrobenzene).

The objective of extraction is to remove by-products, starting materials, and unidentified color bodies, but to retain the desired PAP product in the aqueous phase for separation therefrom by precipitation. The amount of color bodies removed from each extraction is not quantified, but is indicated by the color of the PAP recovered; i.e., the performance is based on recovering pure white stable PAP from the final raffinate after further charcoal treatment.

The extraction results obtained are as shown in Table I below.

TABLE I

Temperature 80° C.

| | Wt. g. | PAP g. | OAP g. | ANL g. | ODA g. | NB g. |
|---|---|---|---|---|---|---|
| Feed Solution | 2201.00 | 143.69 | 10.09 | 37.59 | 1.81 | 8.02 |
| 1st Extract Toluene | 260.70 | | | | | |
| Raffinate 1 | 2144.40 | 144.23 | 8.94 | 15.73 | 0.89 | 0.00 |
| 2nd Extract Toluene | 259.80 | | | | | |
| Raffinate 2 | 2104.40 | 143.54 | 8.83 | 7.63 | 0.56 | 0 |
| 3rd Extract Toluene | 260.50 | | | | | |
| Raffinate 3 | 2077.30 | 140.4 | 8.59 | 3.74 | 0 | 0 |
| 4th Extract Toluene | 259.50 | | | | | |
| Raffinate 4 | 2049.40 | 138.6 | 8.26 | 2.17 | 0 | 0 |
| 5th Extract Toluene | 259.20 | | | | | |
| Raffinate 5 | 2024.20 | 137.51 | 8.21 | 1.47 | 0 | 0 |

What is claimed is:

1. In a process for purifying 4-aminophenol from a reaction mixture from the reduction of nitrobenzene with hydrogen and a hyrdogenation catalyst in aqueous sulfuruc acid, the improvement which comprises
    adding a solvent system consisting of toluene at a temperature of about 75° to 85° C. before or after a pH adjustment of the reaction mixture to about 4.0 to 5.0 wherein the weight ratio of toluene to any aniline present is at least 6.5:1, followed by
    extracting the aqueous layer from the toluene layer at about 75° to 85° C. to remove dissolved impurities.
2. The process of claim 1, wherein the pH is adjusted to 4.6–4.8.
3. The process of claim 1, wherein ammonia is used for said pH adjustment.
4. The process of claim 1, wherein said pH adjustment is carried out at 75–85° C.
5. The process of claim 1, further comprising the step of adding a charcoal decolorizing agent to the reaction mixture after removing the toluene.
6. The process of claim 5, wherein said charcoal decolorizing agent is activated carbon.
7. The process of claim 1, further comprising the step of adding a sodium sulfite type salt selected from the group consisting of sodium hydrosulfite, sodium bisulfite, sodium disulfite or sodium pyrosulfite to the reaction mixture after removing the toluene.
8. The process of claim 1, further comprising the step of adjusting the pH to the range of 6.5 to 8.0 after removing the toluene.
9. The process of claim 8, wherein said pH range of 6.5 to 8.0 is from 7.0 to 7.4.
10. The process of claim 8, further comprising cooling the reaction solution, after adjustment of the pH to a range of 6.5 to 8.0, to below 10° C.
11. The process of claim 10, wherein the temperature of below 10° C. is 0° C. or less.
12. The process of claim 8, wherein ammonia is used for said pH adjustment.

* * * * *

UNITED STATES PATENT AND TRADEMARK OFFICE
CERTIFICATE OF CORRECTION

PATENT NO. : 4,870,209
DATED : September 26, 1989
INVENTOR(S) : Kao et al.

It is certified that error appears in the above-identified patent and that said Letters Patent is hereby corrected as shown below:

Claim 1, Col. 6, line 31 "hyrdogentation" should read:

"hydrogenation"

Claim 1, Col. 6, line 32 "sulfuruc" should read:

"sulfuric"

Signed and Sealed this

Second Day of April, 1991

Attest:

HARRY F. MANBECK, JR.

Attesting Officer

Commissioner of Patents and Trademarks